United States Patent [19]

Vandemoortele

[11] Patent Number: 5,672,166
[45] Date of Patent: Sep. 30, 1997

[54] DISPOSABLE ABSORBENT ARTICLE OF HYGIENE WITH DOUBLE LEAKPROOFING BARRIER AND PROCESS OF MANUFACTURE

[75] Inventor: Philippe Vandemoortele, Lille, France

[73] Assignee: Peaudouce, Linselles, France

[21] Appl. No.: 569,265

[22] PCT Filed: Jul. 8, 1994

[86] PCT No.: PCT/FR94/00857

§ 371 Date: Jan. 5, 1996

§ 102(e) Date: Jan. 5, 1996

[87] PCT Pub. No.: WO95/02381

PCT Pub. Date: Jan. 26, 1995

[30] Foreign Application Priority Data

Jul. 12, 1993 [FR] France ................................ 93 08566

[51] Int. Cl.⁶ .......................... A61F 13/15; A61F 13/20
[52] U.S. Cl. .................... 604/385.2; 604/358; 604/378; 156/164
[58] Field of Search ........................ 604/385.1, 385.2, 604/378, 383; 156/164, 166, 163

[56] References Cited

U.S. PATENT DOCUMENTS 4,662,877  5/1987  Williams .
4,846,825  7/1989  Enloe et al. .

FOREIGN PATENT DOCUMENTS

| 0219326B1 | 4/1987 | European Pat. Off. . |
| 0376022B1 | 7/1990 | European Pat. Off. . |
| 0518044A1 | 3/1992 | European Pat. Off. . |
| 0567105A1 | 10/1993 | European Pat. Off. . |
| 2566631 | 1/1986 | France . |
| 2695314 | 3/1994 | France . |
| 2159693 | 12/1985 | United Kingdom . |
| 2161059 | 1/1986 | United Kingdom . |
| WO 92/22271 | 12/1992 | WIPO . |

*Primary Examiner*—John G. Weiss
*Assistant Examiner*—Ki Yong O
*Attorney, Agent, or Firm*—Burns, Doane, Swecker & Mathis LLP

[57] ABSTRACT

An absorbent article of hygiene with a double leakproofing barrier of simple and economical manufacture includes two side flaps (11) secured together at their transverse ends and a lengthwise fold (16) pointing vertically towards the interior, to form an oblong central opening (17) about the absorbent pad (2) which constitutes a peripheral first leakproofing barrier, the two vertical folds themselves constituting a side second leakproofing barrier.

16 Claims, 2 Drawing Sheets

DISPOSABLE ABSORBENT ARTICLE OF HYGIENE WITH DOUBLE LEAKPROOFING BARRIER AND PROCESS OF MANUFACTURE

BACKGROUND OF THE INVENTION

1. Field of the Invention

The present invention relates to a disposable absorbent article of hygiene, such as a diaper or dressing for the incontinent, of the type comprising an absorbent pad arranged between an impervious outer supporting sheet and a permeable inner sheet.

2. Description of the Invention

More particularly, the present invention relates to such a disposable absorbent article of hygiene comprising a double leakproofing barrier consisting of a peripheral first leakproofing barrier forming a confinement pouch and arranged substantially over the whole periphery of the absorbent pad, supplemented by a second leakproofing barrier made up of two vertical, lengthwise fevers which are situated on each side of the peripheral first barrier.

Articles of hygiene are known, for example, from Patent Application GB-A2 161 059 (Kimberly-Clark). According to this document two leakproofing flaps lie, above the absorbent pad, pointing at each other so that their elasticated distal edges are situated near one another. The leakproofing side flaps are made by a double folding of the liquid-permeable inner sheet covering the liquid-impervious supporting sheet and the absorbent pad secured to this supporting sheet. At their two ends corresponding to the two edges of the diaper the flaps are secured so as to be always turned inwards, one towards the other, without being able to fold outwards, for example when the article of hygiene is put on the user. These side flaps improve the leakproofing of the articles of hygiene in the lateral direction especially in the crotch region. On the other hand, the risks of leakages continue to exist in the two belt regions.

It is furthermore known, for example from Patent Application GB-A2 159 693 (Kimberly-Clark) to provide in each belt region of such an article of hygiene a pouch consisting of a flap extending transversely from a lengthwise edge of the article of hygiene in the direction of the opposite lengthwise edge, it being possible for the innermost edge of this flap to be optionally elasticated. These pouches improve the leakproofing only in the belt regions.

It has already been proposed to improve, in one and the same article of hygiene, both the side leakproofing, especially in the crotch region, and leakproofing in the belt regions. Thus, according to U.S. Pat. No. 4,662,877 (Williams), the inner sheet of such an article of hygiene is covered with an additional sheet comprising above the absorbent pad a rectangular cutout whose two lengthwise edges are elasticated. It should be noted that, according to this document, the additional sheet is secured to the permeable inner sheet along two opposite transverse edges corresponding to the transverse edges of the article of hygiene and along two opposite lengthwise edges situated outside the crotch elastic members of the article of hygiene, which elastic members themselves are situated outside the opposite lengthwise edges of the absorbent pad. Such an additional sheet comprising an opening or rectangular cutout with elasticated lengthwise edges entails a high usage of material, especially because of the discarded material resulting from the formation of the rectangular cutout made in the additional sheet. Now, in the case of disposable absorbent articles of hygiene such as diapers it is essential to reduce as much as possible the quantities of material which is employed and hence the cost of manufacture of the articles.

Patent Application EP-A-0 219 326 (Procter & Gamble) describes a disposable one-piece diaper comprising an impervious supporting sheet, an absorbent pad and a permeable cover sheet covering the pad, this cover sheet being provided with two lengthwise side flaps forming antileakage barriers. These flaps may consist of added strips secured to the supporting sheet along their proximal lengthwise edges and secured to the cover sheet along their distal lengthwise edges near the transverse edges of the diaper. In another embodiment these flaps consist of a double fold of the cover sheet itself, the fold resulting from the double folding being secured along its proximal lengthwise edge to the cover sheet outside the pad and partly along its distal lengthwise edge, near the transverse edges of the diaper to the underlying part of the cover sheet. These side flaps improve the leakproofing of the diaper in the sideways direction, especially in the crotch region. On the other hand, risks of leakages still remain in the belt regions.

To overcome this defect it has also been proposed to add two belt pouches to the structure of the diaper of preceding application. In particular, Patent Application EP-A-0 376 022 (Procter & Gamble) describes the production of such belt pouches which-consist of two added transverse strips. Such a structure complicates the manufacture of the diapers, especially when the latter are manufactured continuously in the lengthwise direction. In addition, this structure increases the usage of material needed for the manufacture of the diaper.

Finally, in Patent Application FR-A 92 10 601 (Peaudouce) a disposable absorbent diaper is proposed comprising an impervious outer supporting sheet, an absorbent pad and a permeable inner cover sheet covering the absorbent pad which comprises two side flaps extending above the absorbent pad so that their proximal edges are joined to the cover sheet along lengthwise lines situated above the lengthwise edges of the absorbent pad, the said lengthwise flaps being joined together at their distal edges from the transverse edges of the diaper at least to the corresponding transverse edges of the absorbent pad, thus to form a peripheral leakproofing barrier over the whole periphery of the pad. No revers or additional side leakproofing barriers are provided in this structure. On the other hand, the opening of the pouch formed by the side flaps is small in width and the width of this opening cannot be variant in the lengthwise direction, unless a cutout of variable width is provided in the flaps, which results in an additional usage of material.

OBJECTS AND SUMMARY

An aim of the present invention is therefore to provide a disposable absorbent article of hygiene, such as a diaper or dressing for the incontinent, comprising a double leakproofing barrier, requiring only a limited usage of material.

An objective of the present invention is also to provide such a disposable absorbent article of hygiene comprising a double leakproofing barrier consisting of a peripheral first leakproofing barrier over the whole periphery of the absorbent pad and forming a confinement pouch supplemented by a side second leakproofing barrier made up of two vertical side revers situated on each side of the peripheral first leakproofing barrier.

Another objective of the present invention is such an absorbent article of hygiene which includes a peripheral leakproofing barrier which forms a confinement pouch, the width of which varies in the lengthwise direction.

An objective of the present invention is also such an absorbent article of hygiene in which the side revers are produced by elasticated folds formed from the flaps themselves and have a determined height.

A further objective of the present invention is such an absorbent article of hygiene in which the height of the folds forming the revers varies lengthwise starting from a maximum height.

Finally, another subject of the present invention is a process for the manufacture of such an absorbent article of hygiene, which is simple and economical to implement.

According to the present invention the disposable absorbent article of hygiene, such as a diaper or a dressing for the incontinent, comprises a liquid-impervious supporting sheet which has opposite lengthwise edges and transverse edges, each of the lengthwise edges comprising an indentation defining a crotch region of reduced width and two end regions of increased width. An absorbent pad of generally rectangular shape and smaller in size than the supporting sheet, is secured to the said supporting sheet. A liquid-permeable inner cover sheet, of generally rectangular shape is secured to the absorbent pad. This cover sheet is of sufficient size to cover the absorbent pad at least in the crotch region.

First lengthwise elastic members are secured, in the stretched state, to the supporting sheet outside the lengthwise edges of the absorbent pad. Two side flaps made of flexible material, for example a hydrophobic nonwoven, of general rectangular shape and of length greater than the length of the absorbent pad, are secured to the supporting sheet symmetrically in relation to a median lengthwise axis of the article. Each of the flaps comprises an intermediate part of a length which is preferably at least equal to the crotch region and smaller than the length of the absorbent pad joining together two end parts. The end parts of a flap are joined to the corresponding end parts of the other flap, along the median lengthwise axis. Each of the intermediate parts of each of the flaps comprises an identical lengthwise fold or fevers of a length which is preferably at least equal to that of the crotch region and of determined height (H), pointing vertically towards the interior of the article and situated above the absorbent pad nearer to the lengthwise edge of the absorbent pad in the crotch region than to the median lengthwise axis. Second elastic members of a length which is preferably at least equal to that of the crotch region are secured, in the stretched state, to the inside of each of the said lengthwise folds. Finally, each of the side flaps is secured to the cover sheet by a lengthwise connecting line situated outside in relation to the said lengthwise fold and preferably above the absorbent pad in the crotch region.

The said intermediate parts thus form together a lengthwise opening of oblong shape above the absorbent pad which forms a peripheral first leakproofing barrier practically over the periphery of the absorbent pad and comprise side revers pointing vertically above the absorbent pad forming a leakproofing second side barrier.

In a recommended embodiment the end parts of the flaps have a width which is greater than half of the width of the supporting sheet so as to have regions which overlap along the median lengthwise axis, these overlapping regions being joined to each other.

The absorbent article of hygiene according to the invention preferably comprises third lengthwise elastic members secured, in the stretched state, along the opening. These third elastic members also preferably have a length which is at least equal to the length of the crotch region and are arranged in lengthwise gussets formed along the lengthwise edges of the opening.

The determined height (H) of the lengthwise folds of each of the flaps can be either uniform over the whole length of the folds or can decrease lengthwise uniformly on either side of a point of maximum height as far as the two ends of the fold. This point of maximum height may be situated in the middle of the fold, that is to say that it divides the fold lengthwise into two equal parts or may be situated at any appropriate place along the length of the fold and, in this case, it divides the fold lengthwise into two unequal parts whose height decreases uniformly towards the ends of the fold. As indicated, the folds of each of the side flaps of the same article are identical, that is to say that they are symmetrical in relation to a vertical plane passing through the median lengthwise axis of the article.

In a particularly recommended embodiment the lengthwise folds are formed by closed loops produced in the intermediate parts of the flaps and are situated nearer to the lengthwise edges of the absorbent pad in the crotch region than to the median lengthwise axis of the article.

When the height (H) of the fold of each of the flaps is uniform over practically the whole length of the fold the intermediate parts of each of the flaps have a reduced width, essentially uniform, in relation to the end parts, over practically their whole length. The intermediate parts thus form an opening of oblong shape over the absorbent pad, of a width which is practically uniform over the whole length of the crotch region. Quite obviously, altering the height of the folds alters the width of the opening and the greater the height (H) of the fold the wider the opening. When the folds have a height which decreases from a point of maximum height the width of the opening will decrease with the decrease in height of the fold starting with a maximum opening width corresponding to the points of maximum height of the folds. The flaps thus form an opening of oval or ovoid shape, symmetrical or asymmetrical in relation to the maximum width of the opening, depending on whether the point of maximum height of the folds divides these folds lengthwise into two equal or unequal parts. It is thus easily possible to produce a Confinement pouch or peripheral barrier whose greatest width is to be found in the appropriate region of the article of hygiene.

The present invention also relates to a process for the manufacture of a flap intended to be employed in an absorbent article of hygiene as described above, which comprises the stages consisting in:

producing a strip of flexible material, preferably of hydrophobic nonwoven, of generally rectangular shape which has a width greater than half of the width of the article of hygiene and similar in length to that of the article of hygiene;

securing lengthwise, in the stretched state, preferably at a distance shorter than half the width of the strip, at least one elastic member over a length which is preferably at least equal to the length of the crotch region of the article;

folding the strip back onto itself around the elastic member of a determined height, to form a loop which has a top and lengthwise side walls whose lower lengthwise edges are distant from the top of the said determined height;

bringing the said lower lengthwise edges of the loop into contact; and joining together the said lower lengthwise edges along a lengthwise connection line in order thus to form a flap which has an intermediate part provided with a fold forming a vertical revers of a length which is preferably at least equal to the length of the crotch region connecting two end parts of greater width.

The lengthwise lower edges of the loop are joined by any appropriate means such as adhesive bonding, heat-sealing and ultrasonic welding.

Quite obviously, depending on the desired final article, the strip will be folded back so as to form a loop of height which is uniform or decreasing lengthwise towards the ends.

The recommended process for the manufacture of the flap additionally comprises a stage consisting in securing lengthwise, another elastic member, in the stretched state, over a length preferably at least equal to the length of the crotch region along a lengthwise edge of the strip.

The lengthwise edge of the strip is also preferably folded back around this other elastic member and is sealed to form a gusset containing the said other elastic member. The production of such an elasticated gusset is conventional and is described in particular in Patent Application FR-A-9210601.

The present invention also relates to a process for securing side flaps to a disposable absorbent article of hygiene comprising a liquid-impervious supporting sheet which has opposite lengthwise edges and transverse edges, each of the lengthwise edges comprising an indentation defining a crotch region of reduced width and two end regions of increased width, an absorbent pad secured to the supporting sheet and smaller in size than the latter, a liquid-permeable cover sheet of general rectangular shape, secured to the absorbent pad and of sufficient size to cover the absorbent pad at least in the crotch region and first lengthwise elastic members secured, in the stretched state, to the supporting sheet outside the lengthwise edges of the absorbent pad, consisting in:

producing two identical flaps as described above;

arranging the flaps thus produced symmetrically in relation to a median lengthwise axis above the supporting sheet, the absorbent pad and the cover sheet, so that the loops are situated above the absorbent pad near the lengthwise edges of the pad in the crotch region and form lengthwise revers pointing vertically towards the interior and situated nearer to the lengthwise edges of the pad in the crotch region than to the median lengthwise axis and so that the corresponding end parts of the said flaps form overlapping regions along the median lengthwise axis;

securing the said flaps over their periphery to the supporting sheet;

securing the said flaps to the cover sheet by means of lengthwise connecting lines preferably situated above the absorbent pad in the crotch region and outside the said loops; and joining the said flaps together in the overlapping regions of the end parts of the said flaps.

An absorbent article of hygiene is thus produced, such as a diaper comprising a double leakproofing barrier made up of a peripheral first leakproofing barrier and of a side second leakproofing barrier, these two barriers being made up by means of only two similar strips of material.

BRIEF DESCRIPTION OF THE DRAWINGS

The continuation of the description, which relates to individual embodiments of the present invention, which are given by way of examples without any limitation being implied, refers to the attached drawings which show, respectively.

DETAIL DESCRIPTION OF PREFERRED EMBODIMENTS

Figure 1:
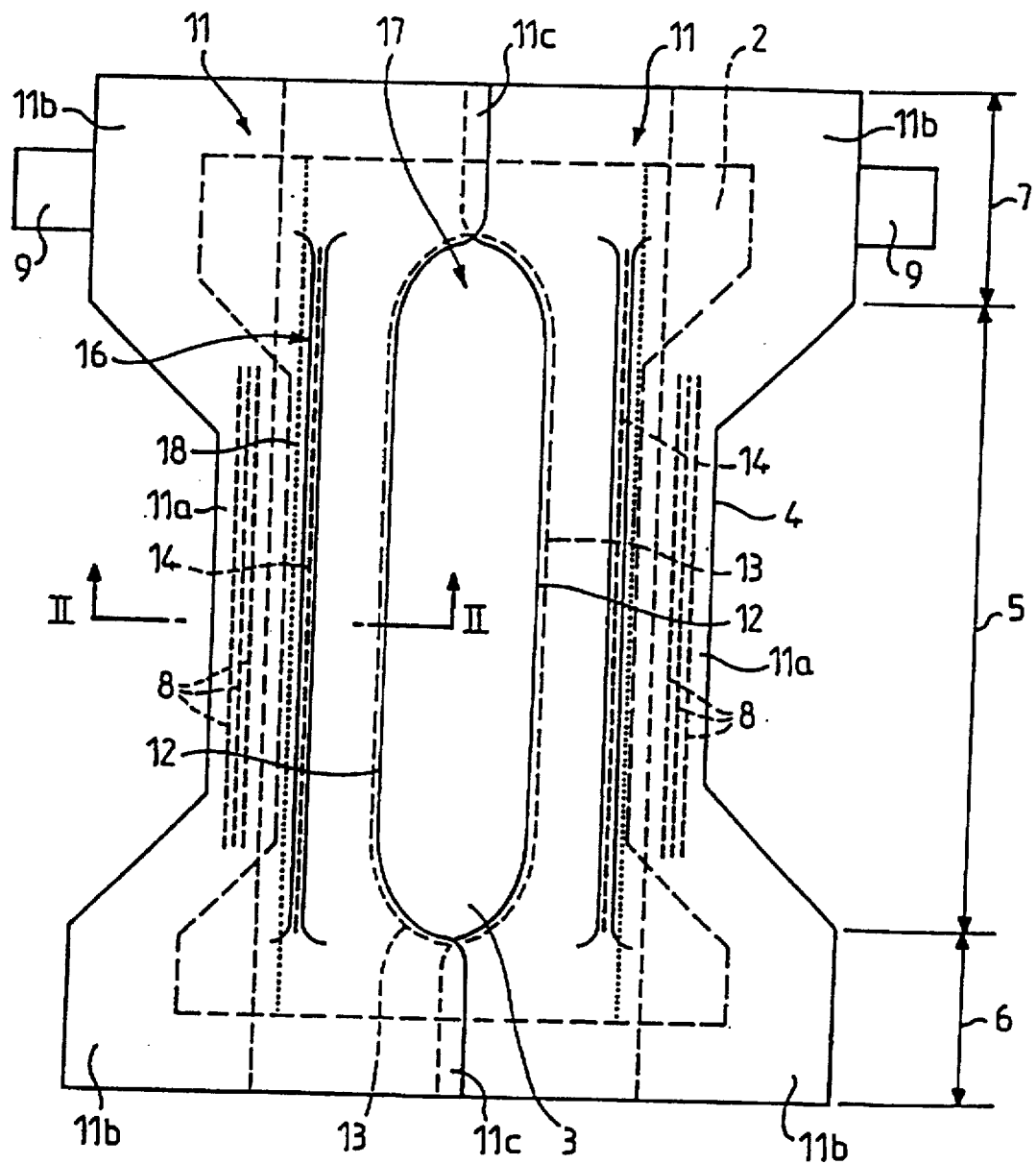
FIG. 1 a top view of a disposable diaper according to the present invention.
Figure 2:
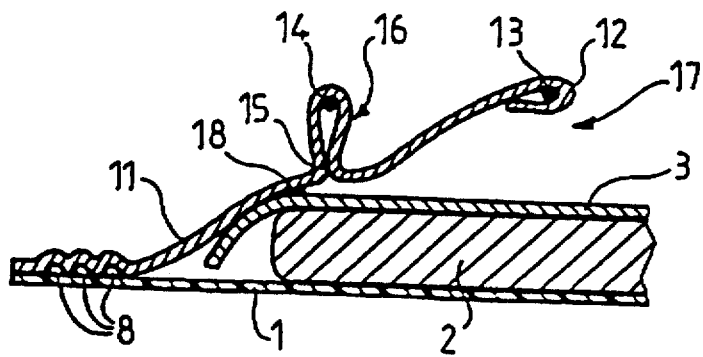
FIG. 2 a view in section made along the line II—II of FIG. 1.

With reference to FIGS. 1 and 2, the diaper according to the present invention comprises conventionally a liquid-impervious outer supporting sheet 1 made, for example, of a thin polyethylene film, a liquid-permeable inner cover sheet 3, for example of hydrophilic nonwoven, and an absorbent pad 2 arranged between the outer supporting sheet 1 and the cover sheet 3.

The impervious supporting sheet 1 is conventionally of an anatomical shape with two indentations 4 defining a crotch region 5 of reduced width and front 6 and rear 7 end parts of increased width. As is also conventional, the absorbent pad is smaller in size than the outer supporting sheet 1 and may have a similar shape, for example an hourglass shape, and is secured to the supporting sheet 1 by any conventional means.

The cover sheet 3 is generally of rectangular shape and has a width which is smaller in relation to the supporting sheet 1 but at least sufficient to be capable of covering the absorbent pad in the crotch region 5, and it is secured to the absorbent pad by lines or regions of adhesive bonding (which are not shown).

This cover sheet 3 generally has a length which is at least equal to the length of the crotch region and at most equal to the total length of the diaper.

The diaper also comprises, in a manner known per se, first crotch lengthwise elastic members 8 and adhesive fastenings 9 on the rear part 7.

The structure described above is conventional and well known in the art.

According to the invention the diaper additionally comprises two side flaps 11 arranged symmetrically in relation to the median lengthwise axis of the diaper, of general rectangular shape and of the same length as the diaper. These flaps 11 are joined to the support sheet along their transverse edges and their proximal lengthwise edge (or periphery) to the corresponding transverse and lengthwise edges of the supporting sheet 1. Each flap comprises an intermediate part 11a of a length at least equal to the length of the crotch region 5 of the diaper which joins two end parts 11b. The end parts 11b of each flap have a length greater than half the width of the diaper so that the corresponding end parts form two overlapping regions 11c along the median lengthwise axis of the diaper. The flaps are joined together in these overlapping regions by any appropriate means, for example by adhesive bonding. The intermediate part 11a of each of the flaps 11 comprises a lengthwise fold or revers 16 of length which is at least equal to the length of the crotch region 5 and preferably smaller than the total length of the absorbent pad 2. These folds or fevers 16 are pointed vertically towards the interior and are situated above the absorbent pad nearer to the lengthwise edges of the pad in the crotch region than to the median lengthwise axis of the diaper. Elastic members 14, preferably similar in length to the folds 16, are secured in the stretched state to the tops of the folds 16 inside the latter. The flaps 11 are additionally secured to the cover sheet 3 by a lengthwise connecting line 18 situated between the lengthwise folds or revers 16 and the lengthwise edge of the pad 2 in the crotch region, preferably along the lengthwise edge of the pad 2 in the crotch region 5. Thus, the lengthwise folds 16 are situated between the lengthwise connecting lines 18 and the distal lengthwise edges 12 of the flaps.

In the recommended embodiment shown the intermediate parts 11a of the flaps 11 are of a length which is greater than the length of the crotch region but smaller than the length of the pad, so that the overlapping regions 11c of the intermediate parts 11b are extended from the transverse edges of the diaper as far as the transverse edges of the absorbent pad.

In the embodiment shown, the folds or revers 16 of each of the flaps have a height H which is practically uniform over their whole length so that the distal lengthwise edges 12 of the flaps together form over a major part of their length an opening of oblong shape of practically uniform width over a major part of its length. This opening constitutes a peripheral first leakproofing barrier forming a confinement pouch.

Elastic members 13 are secured in the stretched state along at least one major part of the distal lengthwise edges 12 of the flaps 11. In the embodiment shown the distal lengthwise edges 12 of the flaps are folded back and adhesively bonded to form gussets in which the elastic members 13 are secured in the stretched state, preferably at their ends, for example by adhesive bonding.

The elastic members may consist of a single strand or of a number of parallel strands.

As indicated above, the presence of the folds or revers 16 in the flaps 11 moves the distal lengthwise edges 12 of the flaps 11 away from each other, except near the mutually joined overlapping regions of the end parts, thus creating an opening of oblong shape 17. This opening constitutes a peripheral first leakproofing barrier over the periphery of the absorbent pad, in fact forming a confinement pouch. Furthermore, the folds or revers 16 themselves, which are pointed vertically towards the interior of the diaper and which are situated on either side of the opening 17 constitute a side second leakproofing barrier situated outside in relation to the peripheral first leakproofing barrier forming a confinement pouch. With the construction described above a double leakproofing barrier is therefore obtained comprising a peripheral first leakproofing barrier forming a confinement pouch and a side second leakproofing barrier outside the first leakproofing barrier by means of only two side flaps and consequently with a minimum usage of material.

The folds or revers 16 formed in the flaps 11 may have a height which is uniform over their whole length or a height which varies from a maximum value to a minimum value at the ends of the folds. Furthermore, depending on the lengthwise position of the height of maximum value of the fold, the shape and the width of the opening 17 vary correspondingly.

Figure 3:
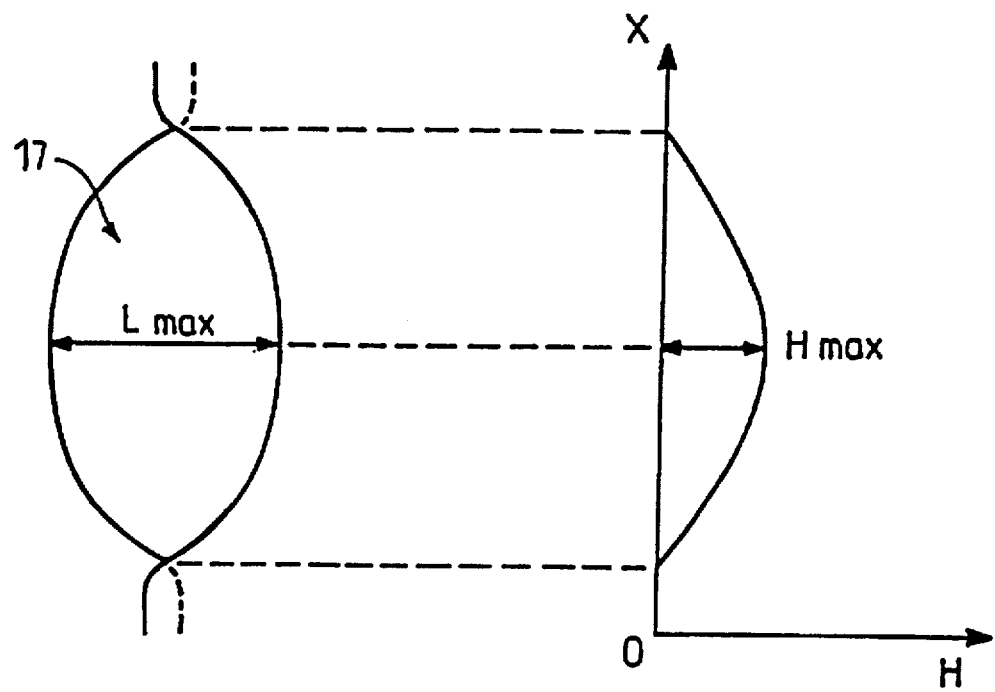
FIGS. 3 and 4 diagrams showing the variation in shape and width of the opening of the peripheral leakproofing barrier as a function of the height of the folds or revers of the flaps.
Figure 4:
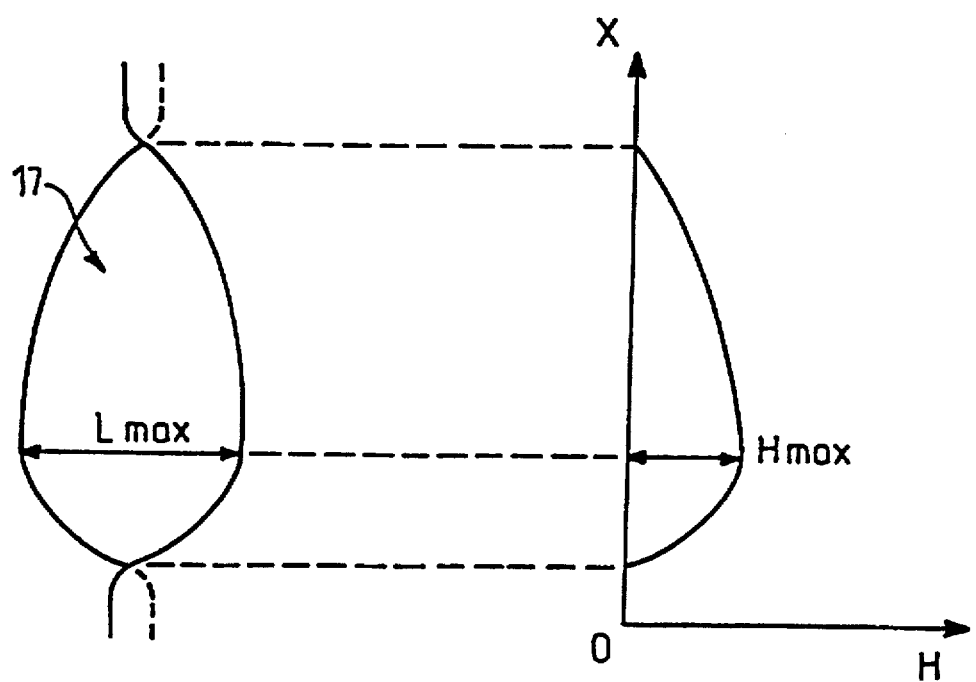

FIGS. 3 and 4 show the variations in shape and width of the opening 17 as a function of the variation in the height of the fold. In the figures the value of the height of the fold has been plotted as abscissa and the lengthwise position as ordinate.

With reference to FIG. 3, a fold 16 has been produced whose maximum height is situated in the middle of the fold and divides this fold into two equal parts whose height decreases uniformly from the point of maximum height as far as the ends of the fold. Correspondingly, the opening 17 will have the symmetrical, generally oval, shape shown whose maximum width is situated in the middle corresponding to the point of maximum height of the folds 16. The width of the opening 17 decreases uniformly on either side of this central maximum width of the opening as far as the overlapping parts 11c of the flaps 11.

FIG. 4 shows the opening 17 corresponding to the folds 16 whose point of maximum height is situated nearer one of the ends of the fold. In this case the point of maximum height of the folds divides each of the folds into two unequal lengthwise parts, the shorter part having a height which decreases more rapidly as far as the corresponding end than the longer part. Correspondingly, the opening 17 will exhibit an offset maximum width aligned transversely with the points of maximum height of the folds 16, thus forming an oblong opening of general ovoid shape whose width decreases uniformly but differently towards the overlapping regions 11c from a maximum value corresponding to the decrease in height of the folds from the point of maximum height.

Thus, by varying the maximum height of the folds and the lengthwise position of this maximum height in the folds it is possible to vary the shape and the width of the opening of the peripheral leakproofing barrier so as to arrange the maximum width of the opening in the appropriate place depending on the envisaged use of the diaper. For example, an opening which is wider towards the front can be provided for diapers intended for boys and an opening which is wider towards the center or towards the rear for girls.

This result is obtained simply with the construction of the present invention with the aid of only two side flaps without it being necessary to make cutouts or to add additional members thereto.

It will be noted that in the present description the expressions "inner" and "outer" as employed to define the relative positions of the different constituent members of the article refer to an article worn by a user, the inner direction being that pointing towards the user and the outer direction being, quite obviously, that pointing moving away from the user.

I claim:

1. A disposable absorbent article of hygiene, such as a diaper or dressing for the incontinent, comprising:
    a liquid-impervious supporting sheet which has opposite lengthwise edges and transverse edges, each of the lengthwise edges comprising an indentation defining a crotch region of a width narrower than two end regions of increased width;
    an absorbent pad secured to the supporting sheet and smaller in size than the supporting sheet;
    a liquid-permeable cover sheet of substantially rectangular shape, secured to the absorbent pad and of sufficient size to cover the absorbent pad at least in the crotch region;
    first lengthwise elastic members secured, in a stretched state, to the supporting sheet outside lengthwise edges of the pad;
    two side flaps made of flexible material, of substantially rectangular shape and of a length greater than a length of the pad and which are secured to the supporting sheet symmetrically in relation to a median lengthwise axis of the article;
    each of the flaps comprises an intermediate part of a length which is at least substantially equal to the crotch region and smaller than the length of the absorbent pad, joining together two end parts;
    the end parts of one of the flaps are joined to the end parts of another of the flaps along the median lengthwise axis;
    the intermediate parts of each of the flaps comprise an identical lengthwise fold of a length which is at least substantially equal to that of the crotch region pointing vertically towards an interior of the article and situated above the absorbent pad nearer to corresponding lengthwise edge of the absorbent pad than to the median lengthwise axis;
    second elastic members of a length which is at least substantially equal to that of the crotch region are secured, in a stretched state, to an inside of each of the lengthwise folds;

each of the said flaps is secured to the cover sheet by a lengthwise connecting line situated substantially outside in relation to the lengthwise fold and above the pad in the crotch region;

so that the opposite lengthwise edges of said intermediate parts of the flaps form together on a major part of their length a lengthwise opening of oblong shape above the absorbent pad, this opening forming a first peripheral leakproofing barrier and said folds forming a second leakproofing barrier situated outwardly with respect to said first barrier.

2. Article according to claim 1, wherein the end parts of the flaps have a width which is greater than half of the width of the supporting sheet so that the corresponding end parts of said flaps have overlapping regions along the median lengthwise axis, said overlapping regions being joined together.

3. Article according to claim 1, wherein each flap additionally comprises third lengthwise elastic members secured, in the stretched state, along the opening.

4. Article according to claim 1, wherein a height of each of the folds is uniform over a whole length of the fold.

5. Article according to claims 1, wherein a height of each of the folds decreases uniformly lengthwise on either side from a point of maximum height to the ends of the fold.

6. Article according to claim 5, wherein the point of maximum height divides the fold lengthwise into two equal parts.

7. Article according to claim 5, characterized in that the point of maximum height divides the fold (16) lengthwise into two unequal parts.

8. Article according to claim 1, wherein the folds include a closed loop.

9. A process for the manufacture of flaps intended to be employed in an absorbent article of hygiene comprising a liquid-impervious supporting sheet which has opposite lengthwise edges and transverse edges, each of the lengthwise edges comprising an indentation defining a crotch region of a narrower width than two end regions of increased width, an absorbent pad secured to the supporting sheet and smaller in size than the supporting sheet, a liquid-permeable cover sheet of substantially rectangular shape, secured to the absorbent pad and of sufficient size to cover the absorbent pad at least in the crotch region and first lengthwise elastic members secured, in a stretched state, to the supporting sheet, outside the lengthwise edges of the absorbent pad, comprising the steps of:

producing a strip of flexible material of substantially rectangular shape which has a width slightly greater than half of a width of the article of hygiene and similar in length to that of the article of hygiene;

securing an elastic member lengthwise, in the a stretched state, at a distance smaller than half of the width of the strip, over a length at least substantially equal to the crotch region of the article;

folding the strip back onto itself around the elastic member, to form a loop which has a top and lengthwise side walls;

bringing the lengthwise lower edges of the loop into contact; and joining together the lengthwise lower edges along a lengthwise connection line in order to form a flap which has an intermediate part provided with a vertical fold of a length which is at least substantially equal to that of the crotch region of the article, joined to two end parts of greater width.

10. Process according to claim 9, wherein the lower edges of the loops are joined by adhesive bonding, heat-sealing or ultrasonic welding.

11. Process according to claim 9, wherein the strip consists of a hydrophobic nonwoven material.

12. Process according to claim 9, wherein height to which the strip is folded hack is uniform.

13. Process according to claim 9, wherein height to which the strip is folded back decreases uniformly from a point of maximum height.

14. Process according to claim 13, wherein the point of maximum height divides the loop lengthwise into two equal parts.

15. Process according to claim 13, wherein the point of maximum height divides the loop lengthwise into two unequal parts.

16. A process for securing side flaps to an absorbent article of hygiene, comprising:

a liquid-impervious supporting sheet which has opposite lengthwise edges and transverse edges, each of the lengthwise edges comprising an indentation defining a crotch region of a narrower width than two end regions of increased width;

an absorbent pad secured to the supporting sheet and smaller in size than the supporting sheet;

a liquid-permeable cover sheet of substantially rectangular shape, secured to the absorbent pad and of sufficient size to cover the absorbent pad at least in the crotch region;

first lengthwise elastic members secured, in a stretched state, to the supporting sheet outside the lengthwise edges of the pad; the process comprising the steps of:

producing two identical flaps;

arranging the flaps thus produced symmetrically in relation to a median lengthwise axis of the article above the supporting sheet, the absorbent pad and the cover sheet, so that loops are pointing vertically towards an interior and are situated nearer to the lengthwise edges of the pad in the crotch region than to a median lengthwise axis and corresponding end parts of the flaps form overlapping regions along the median lengthwise axis;

securing the flaps over their periphery to the supporting sheet;

securing the flaps to the cover sheet by means of lengthwise connecting lines situated substantially above the absorbent pad in the crotch region and outside in relation to the loops; and joining the flaps together in the overlapping regions of the end parts of the said flaps.

* * * * *